(12) United States Patent
Lavoie

(10) Patent No.: US 7,348,452 B2
(45) Date of Patent: Mar. 25, 2008

(54) LIQUID PHASE OXIDATION OF P-XYLENE TO TEREPHTHALIC ACID IN THE PRESENCE OF A CATALYST SYSTEM CONTAINING NICKEL, MANGANESE, AND BROMINE ATOMS

(75) Inventor: Gino Georges Lavoie, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 126 days.

(21) Appl. No.: 10/743,624

(22) Filed: Apr. 22, 2004

(65) Prior Publication Data

US 2005/0240055 A1  Oct. 27, 2005

(51) Int. Cl.
*C07C 51/16* (2006.01)
*C07C 63/00* (2006.01)

(52) U.S. Cl. ............... 562/412; 562/416; 562/417; 562/480

(58) Field of Classification Search .......... 562/416, 562/412, 417, 480; 502/102, 169, 170
See application file for complete search history.

(56) References Cited

U.S. PATENT DOCUMENTS 2,833,816 A    5/1958  Saffer et al.
4,160,108 A *  7/1979  Shigeyasu et al. .......... 562/416
4,786,753 A    11/1988 Partenheimer et al.
5,359,133 A    10/1994 Nazimok et al.
6,476,257 B1 * 11/2002 Park et al. .................. 562/412
6,486,257 B1   11/2002 White et al.

FOREIGN PATENT DOCUMENTS

EP       0041784 A1    12/1981

OTHER PUBLICATIONS

International Search Report.

* cited by examiner

*Primary Examiner*—Taylor Victor Oh
(74) *Attorney, Agent, or Firm*—Bernard J. Graves, Jr.; Jennifer R. Knight

(57) ABSTRACT

A method for liquid phase oxidation of p-xylene with molecular oxygen to terephthalic acid that minimizes solvent loss through solvent burn and minimizes the formation of incomplete oxidation products such as 4-carboxybenzaldehyde (4-CBA). P-xylene is oxidized at a temperature in the range of 120° C. to 250° C. and in the presence of a source of molecular oxygen and a catalyst composition substantially free of zirconium atoms comprising a source of nickel (Ni) atoms, a source of manganese (Mn) atoms, and a source of bromine (Br) atoms, to form a crude reaction mixture comprising terephthalic acid and incompletely oxidized reaction products comprising 4-CBA, wherein the stoichiometric molar ratio of bromine atoms to manganese atoms is 1.5 or less, and the amount of nickel atoms is at least 500 ppm.

21 Claims, 1 Drawing Sheet

Figure 1:
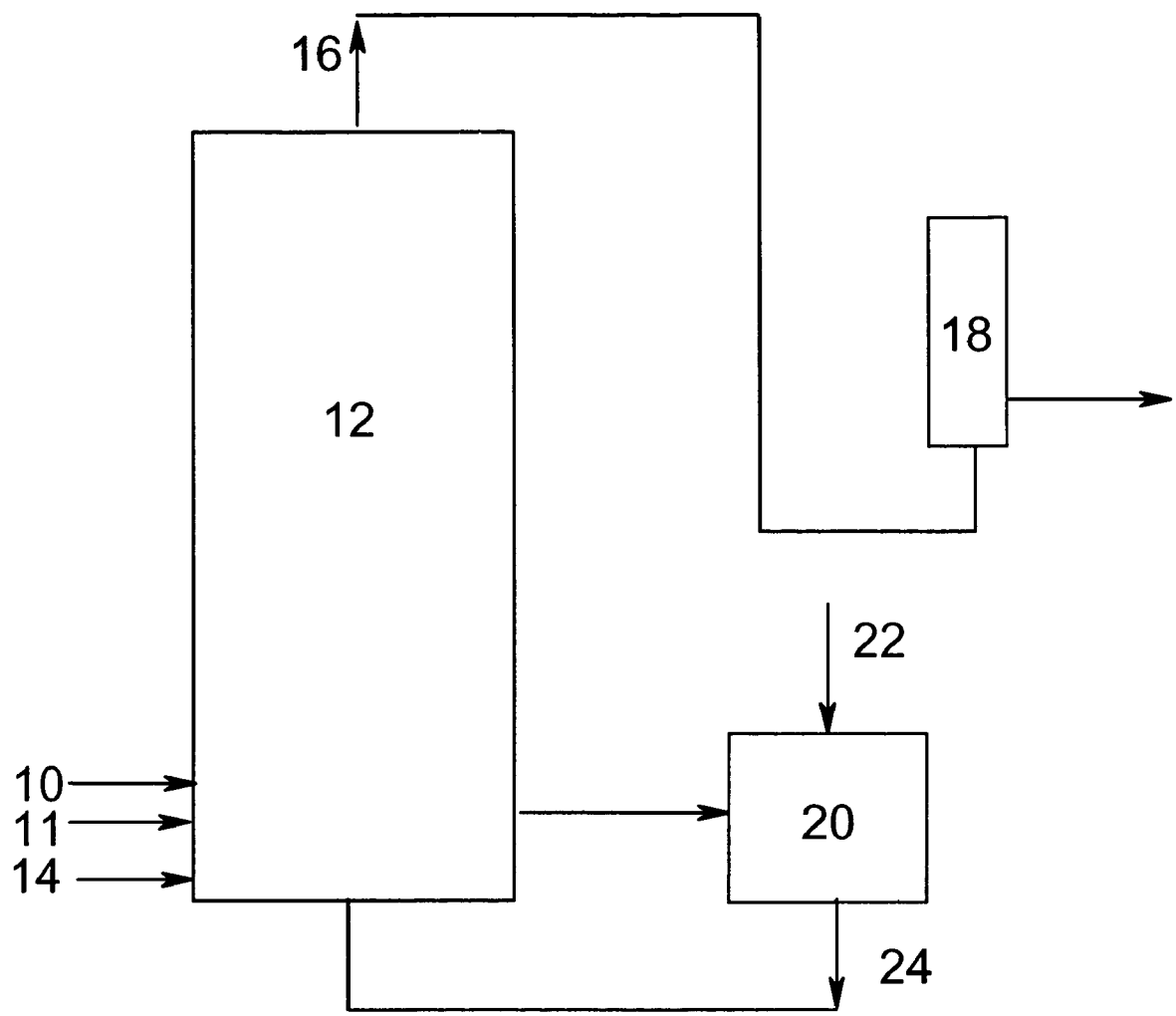

LIQUID PHASE OXIDATION OF P-XYLENE TO TEREPHTHALIC ACID IN THE PRESENCE OF A CATALYST SYSTEM CONTAINING NICKEL, MANGANESE, AND BROMINE ATOMS

1. FIELD OF THE INVENTION

The invention pertains to the liquid phase oxidation of p-xylene, more particularly to the liquid phase oxidation of p-xylene in the presence of a catalyst system containing nickel, manganese, and bromine atoms substantially free of zirconium atoms.

2. BACKGROUND OF THE INVENTION

In typical known processes for producing terephthalic acid, p-xylene is oxidized to the product terephthalic acid. P-xylene is continuously or batchwise oxidized in a primary oxidation reactor in the liquid phase in the presence of an oxygen containing gas such as air. P-xylene, an oxidation catalyst, a molecular source of oxygen, and a solvent such as acetic acid are combined in a reactor to produce a crude terephthalic acid composition. A typical oxidation catalyst composition is made by contacting a cobalt compound with a manganese compound, usually also in combination with a promoter such as a bromine compound.

The resulting terephthalic acid product is not very soluble in a solvent such as acetic acid under the reactor operating conditions, and usually crystallizes out of the solvent as a solid to form a suspension. The crude terephthalic acid composition in the primary oxidation reactor is a reaction mixture which contains terephthalic acid solids, a solvent acting as the suspending medium for the solids and containing a small amount of terephthalic acid dissolved therein, catalyst, unreacted p-xylene, incompletely oxidized intermediate oxidation products such as para-tolualdehyde, para-toluic acid, 4-carboxybenzaldehyde (4-CBA), and other organic impurities which may cause discoloration dissolved in the solvent. The crude terephthalic acid composition is discharged from the oxidation zone and generally subjected to a variety of mother liquor exchange, separation, purification, and recovery methods, resulting in recycling back to the oxidation zone the recovered solvent and catalyst composition. It would be desirable to reduce the amount of incompletely oxidized intermediates ("intermediates"). By reducing the amount of intermediates, primarily composed of 4-CBA, one may either improve the yield, reduce the volume of mother liquor containing the intermediates which must be separated from the terephthalic acid product, reduce the amount of intermediates needed in a post oxidation reactor, or all the foregoing.

Other by-products of the liquid phase oxidation which are partially or completely removed from the reaction mixture in the oxidation reactor are the off-gases which include water, solvent, unreacted oxygen and other unreacted gases found in the source of the molecular oxygen gas such as nitrogen and carbon dioxide, and additional amounts of carbon dioxide and carbon monoxide produced by the catalytic decomposition of the solvent under the oxidation conditions. The off-gases are vented at the overhead of the oxidation reactor to a distillation column or a condenser to separate the solvent from the other off-gases such as water, carbon dioxide, carbon monoxide, nitrogen, methyl bromides, etc. The solvent recovered in the distillation column or condensers is recycled back to the oxidation reactor for further use. The hot uncondensed gases are removed from the distillation column and sent to energy recovery devices, such as turboexpanders and electric generators, or to heat exchangers, or to steam generators, optionally before or after passing through catalytic oxidation or other suitable equipment for neutralizing or removing acidic and corrosive ingredients in the gaseous stream.

The oxidative decomposition of the solvent in the primary oxidation reactor resulting in the generation of carbon dioxide and carbon monoxide gas is referred to as the solvent burn, and results in the loss of solvent. It is desirable to recover and recycle back to the oxidation reactor as much solvent as possible for further use. However, once the solvent is decomposed in the primary oxidation reactor into its constituent gaseous products, such as carbon monoxide and carbon dioxide when acetic acid is the solvent, there no longer exists solvent to recover resulting in the permanent loss of solvent and requiring a fresh source of make-up solvent. Reducing the amount of solvent burn would significantly lower the operating costs in the oxidation zone by allowing a greater amount of solvent to be recovered and recycled back to the oxidation zone and by lowering the amount of fresh make-up feed. However, the reduction in solvent burn should not come at the expense increasing the amount of 4-CBA in the crude mixture, and if possible, it would be desirable to simultaneously reduce the solvent burn and reduce the amount of 4-CBA generated in the crude oxidation mixture.

3. SUMMARY OF THE INVENTION

We have found that the decomposition of a solvent in an oxidation process and the production of 4-CBA can be controlled by a combination of an appropriate selection of reaction conditions and catalyst composition. There is now provided a process for the oxidation of p-xylene to terephthalic acid comprising oxidizing in the liquid phase a p-xylene composition comprising at least 80 wt. % p-xylene based on the weight of liquid reactants, at a temperature in the range of 120° C. to 250° C. and in the presence of a source of molecular oxygen and a catalyst composition substantially free of zirconium atoms comprising a source of nickel (Ni) atoms, a source of manganese (Mn) atoms, and a source of bromine (Br) atoms, to form a crude reaction mixture comprising terephthalic acid and incompletely oxidized reaction products comprising 4-carboxybenzaldehyde compounds, wherein the stoichiometric molar ratio of bromine atoms to manganese atoms is 1.5 or less, and the amount of nickel atoms is at least 500 ppm.

There is also provided a catalyst composition substantially free of zirconium atoms comprising a source of nickel atoms, a source of manganese atoms, and a source of bromine atoms, wherein the molar ratio of bromine atoms to each of nickel atoms and manganese atoms are 1.5 or less, and the amount of nickel atoms are at least 500 ppm. The catalyst composition is also preferably substantially free of cobalt atoms.

4. BRIEF DESCRIPTION OF THE DRAWINGS

FIG. 1 illustrates a process flow of crude terephthalic acid streams and the overhead of an oxidation unit.

5. DETAILED DESCRIPTION OF THE INVENTION

It is to be understood that the word comprising is open ended and may include any number and type of unstated steps, processes, or ingredients. The description of method steps does not preclude intervening steps and is not restricted to carrying out the steps in a particular order unless otherwise stated. Numerical ranges include each integer and all fractions thereof between the end points of the stated range.

The process comprises oxidizing p-xylene in the liquid phase. The liquid phase may at any moment comprise the feed reactants, or the carboxylic acid reaction product dissolved or suspended in the reaction mixture, or both, especially in a continuous process.

The product of the oxidation of p-xylene includes terephthalic acid solids as the predominant product (at least 50 wt. % of the solids), and incomplete oxidation products which may be found in the solids, in the liquid phase, or in both. P-xylene fed to the oxidation reactor may be purified of contaminants which may interfere with the oxidation reaction. The reactant feed may be pure or a mix of the compounds isomers or lower or higher homologues, as well as some saturated alicyclic or aliphatic compounds having similar boiling points to the aromatic or fused ring compounds. However, at least 80 wt. %, preferably at least 95 wt. %, or at least 98 wt. % of the liquid reactants is p-xylene.

In one embodiment of the invention, the liquid phase oxidation process is carried out in the presence of a solvent. Suitable solvents are those which are solvents for the p-xylene under the oxidation reaction conditions, wherein the p-xylene is sufficiently soluble in the solvent so as to be completely soluble therein or sufficiently soluble to form a pumpable crude flow discharged from the oxidation reactor. Suitable solvents include water and the aliphatic solvents. The preferred aliphatic solvents are aliphatic carboxylic acids which include, but are not limited to, aqueous solutions of $C_2$ to $C_6$ monocarboxylic acids, e.g., acetic acid, propionic acid, n-butyric acid, isobutyric acid, n-valeric acid, trimethylacetic acid, caprioic acid, and mixtures thereof. Preferably, the solvent is volatile under the oxidation reaction conditions to allow it to be taken as an off-gas from the oxidation reactor. It is also preferred that the solvent selected is also one in which the catalyst composition is soluble under the reaction conditions.

The most common solvent used for the oxidation of p-xylene is an aqueous acetic acid solution, typically having a concentration of 80 to 99 wt. %. In especially preferred embodiments, the solvent comprises a mixture of water and acetic acid which has a water content of about 2.5% to about 15% by weight. Additionally, a portion of the solvent feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 2.5 to 15% water. This exchange may be accomplished in any convenient apparatus but can most easily be accomplished in a centrifuging apparatus, such as one or more cyclones.

The amount of solvent used in not limited. It is not generally necessary to use large amounts. Suitable amounts of solvent range from 0.1 wt. % to 20 wt. %, or 1 wt. % to 10 wt. %, or even small amounts in the range of 1 wt. % to 5 wt. %, based on the weight of all feeds to the oxidation reaction zone.

The oxidation of p-xylene is conducted in the presence of a source of oxygen. This is easily accomplished be feeding an oxygen containing gas to the primary oxidation reactor to allow the gas to contact the liquid reaction mixture in the reactor. Preferred oxygen containing gases include air and other mixtures of nitrogen and oxygen. One such convenient mixture which can be used in the process of the present invention is the vent gas from the primary oxidation which ordinarily comprises about 5 to 20% oxygen. By reducing the amount of oxygen in the gas to a level less than found in air, the extent of solvent burn can be further reduced in the primary oxidation zone and also in secondary post oxidation reactors further downstream designed to complete the oxidation of intermediate products produced in the primary oxidation reactor.

The relation between the temperature and pressure in the primary oxidation reactor is regulated to ensure that the reaction proceeds essentially in the liquid phase rather than completely in the gaseous phase, while allowing the reaction to proceed towards the oxidation of the reactants. The p-xylene feed should not be mostly vaporized. Thus, the oxidation reaction proceeds at elevated temperatures and pressures. It is desirable to ensure that at least 70% of the reactants remain in the liquid phase, more preferably at least 80%. The oxidation reaction desirably proceeds at a temperature ranging from 80° C. to 250° C., and the heat of reaction will generate pressures ranging from 70 psig to 800 psig. For example, as p-xylene is oxidized to produce TPA using the catalyst composition of the invention in a liquid phase oxidation carried out at a temperature ranging from 120-200° C. and a pressure in the range of about 90 to 270 psig. Lowering the oxidation temperature also helps to reduce the extent of solvent burn, all other conditions and ingredients being equal. The process of the invention is particularly well suited for oxidizing p-xylene at low temperatures without generating excessive amounts of 4-CBA. Thus, more preferred oxidation temperatures are within the range of 140° C. to 190° C.

The catalyst system employed in the process of the invention is substantially free of zirconium atoms and comprises a source of nickel atoms, a source of manganese atoms, and a source of bromine atoms. The catalyst composition is preferably soluble in the solvent under reaction conditions, or it is soluble in the reactants fed to the oxidation zone. More preferably, the catalyst composition is soluble in the solvent at 40° C. and 1 atm., and is soluble in the solvent under the reaction conditions.

The source of nickel may be provided in ionic form as inorganic nickel salts, such as nickel nitrate, nickel chloride, or organic nickel compounds such as nickel salts of aliphatic or aromatic acids having 2-22 carbon atoms, including nickel acetate, nickel octanoate, nickel benzoate, and nickel naphthalate. The weight amount of each of nickel, manganese, bromine, or other atoms are based on the atomic weight of the atom, whether or not the atom is in elemental form or in ionic form. The weight percentage of a catalyst component includes the counter-cation or anion only if the weight percentage is used in the context of the source of the atom. For example, the amount of nickel refers to the amount of nickel atoms, whether elemental or ionic, and not the amount of nickel acetate. The stated concentration of catalyst components are based on the quantity of catalyst components in the reaction zone of the oxidation reactor. The catalyst component concentrations can be measured by sampling the oxidation reactor underflow.

Nickel in the catalyst composition may be present in a concentration of about 500 to 5000 ppm, based on the weight of all liquid and solid feeds. Preferably, the concentration of nickel is about 500 to 4000 ppm. Even more preferably, the concentration of nickel is about 1500 to 3000 ppm. The oxidation state of nickel when added as a compound to the reaction mixture is not limited, and includes +2 or +3.

The source of manganese may be provided as inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate. Manganese in the catalyst composition may be present in a concentration of about 100 to 3000 ppm. Preferably, the concentration of manganese is about 200 to 2500 ppm.

The bromine component may be added as elemental bromine, in combined form or as an anion. Suitable sources of bromine include hydrobromic acid, sodium bromide, ammonium bromide, potassium bromide, tetrabromoethane, benzyl bromide, 4-bromopyridine, alpha-bromo-p-toluic acid, and bromoacetic acid. Hydrogen bromide and alpha-bromo-p-toluic acid are preferred bromine sources. Bromine in the catalyst composition may be present in an a mount ranging from 150 to 3000 ppm, based on the total liquid.

The catalyst composition of the invention is substantially free of zirconium, and preferably also substantially free from cobalt. In one embodiment, the catalyst composition is free of any metals other than nickel and manganese. We have found that zirconium added to the catalyst composition impairs the reduction of solvent burn. For example, the solvent burn in an oxidation reaction is much higher using a catalyst composition containing Mn, Ni, Zr, and Br compared to the solvent burn observed when only Mn, Ni, Br are used the catalyst composition. Thus, the catalyst composition is devoid of Zr in a quantity which would increase the solvent burn by more than 10% relative to the same catalyst composition devoid of Zr. In one embodiment, the catalyst composition contains less than 5 ppm Zr, or 2 ppm or less of Zr, or 0 ppm Zr. Likewise, in another embodiment, the catalyst composition further contains less than 5 ppm cobalt, or 2 ppm or less of cobalt, or 0 ppm cobalt.

The relative amounts of elements in the catalyst composition are not particularly limited, other than molar amount of bromine relative to manganese atoms is 1.5 or less. Normalizing the molar quantity of manganese to 1, the molar amount of bromine is 1.5 or less, preferably 1.1 or less, or 1.0 or less, and even 0.9 or less.

In a preferred embodiment, the molar amount of bromine relative to each of nickel and manganese is 1.5 or less, or 1.1 or less, or 1.0 or less, or 0.9 or less. The molar amount of bromine is desirably at least 0.3, or 0.5 relative to the molar amount of each of nickel and manganese in order to maximize the yield of the desired acid.

Suitable molar stoichiometric ratios of the nickel atoms to manganese atoms range from 0.2:1 to 4:1, preferably about 0.5:1 to 2.5:1.

Non-limiting examples of catalyst component molar ratios suitable for use in the invention include the following: molar stoichiometric ratios of nickel atoms to bromine atoms ranging from about 0.66:1 to 5:1, or about 0.9:1 to 4:1, or a bout 1.0:1 to 3.5:1, or about 1.1:1 to 3.5:1; and molar stoichiometric ratio of manganese atoms to bromine atoms ranging from about 0.67:1 to 5:1, or 0.9:1 to 2.5:1, or about 1.0:1 to 2:1, or about 1.1:1 to 1.8:1. Other suitable ranges include, by way of example, molar stoichiometric ratios of the following metals: $Ni_{1-2.5}Mn_{1-2}Br_{0.3-1.5}$ or $Ni_{1-2.5}Mn_{1-2}Br_{0.6-1}$.

The particular amount of nickel used in the catalyst composition is at least 500 ppm Ni to be effective to maximize the yield of the desired acid. Below this amount, the yield to the desired acid suffers significantly.

The total amount of catalyst present in the primary oxidation reactor, based on the ppm by weight of Ni, Mn, and Br atoms, and any other added metal atoms relative to the weight of the solvent is effective to obtain the desired degree of conversion at the operation temperature. In general, suitable amounts of catalyst range from 2000 ppm to 9000 ppm of total combined metal and bromine atoms, although more can be used if desired, especially if the oxidation reaction is conducted at lower temperatures. Suitable amounts of catalyst based on their compound weight will vary widely depending on the counter ion molecular weight, but for most common anions, the amounts would generally range from 0.1 to 10 wt %, or 0.1 to 5 wt. %, or 0.1 to 3 wt. %, based on the weight of the solvent.

Other organic or non-metallic catalyst components can be included in the catalyst composition of the invention. For example, the catalyst composition may include a source pyridine. The pyridine component of the catalyst system may be added to a primary oxidation reactor or to post oxidation reactors. The pyridine component can be in the form of pyridine per se or the form of a compound of pyridine. For example, 4-bromopyridine may be used as both a source of pyridine and bromine atoms.

The catalyst composition can be formed by adding each source of metal and bromine atoms of the catalyst composition to the oxidation reactor separately in sequence or simultaneously, or a prepared composition may be added to the oxidation reactor, and in either case, the addition may be made as an initial batch or continuously during the course of the oxidation reaction. The catalyst composition prepared as a batch may be dissolved in the solvent to form a catalyst feed followed by adding the catalyst feed to the primary oxidation reactor. Each component, or the catalyst composition batch, can be added to the primary oxidation reactor before or after or during addition of the solvent. In a continuous process, the catalyst components or the catalyst composition are added simultaneous with the solvent feed, or in the solvent feed, or separately metered as required for fresh make-up.

After the initial charge of catalyst composition in a continuous process, the residual mother liquor from the primary oxidation supplies a portion of the necessary catalyst components to the primary oxidation reactor by partial displacement of the primary oxidation mother liquor with fresh solvent. The remainder can be made up with a continuous fresh feed of make-up catalyst.

By using the catalyst composition of the invention, the extent of solvent burned and rendered unusable in a recycle stream is reduced relative to other catalyst compositions containing zirconium, or other catalyst compositions containing the same metal atoms with molar quantities of bromine in excess of 1.5 with respect to manganese, under identical operating conditions. While the absolute amount of solvent burn in the present invention is quite low, this reduction is not achieved at the expense of yield. Obtaining a low amount of solvent is possible by running the reaction at low oxidation temperatures or using a catalyst which has a lower degree of conversion or selectivity, but this negatively impacts other results such as lowered yields and increased quantities of intermediates. The catalyst composition of the invention has the advantage of a maintaining a low ratio of solvent burn to yield, thereby minimizing the impact on yield to obtain the low solvent burn relative to other catalyst compositions while simultaneously generating low quantities of incomplete intermediate oxidations products.

In a preferred embodiment, the ratio of solvent burn (in moles of CO and $CO_2$ expressed as $CO_x$, per mole of terephthalic acid produced) is 0.80 moles $CO_x$/mol TPA or less, or 0.70 or less, or 0.55 or less.

The catalyst composition of the invention is also capable of reducing the quantity of incomplete intermediate oxidation products produced in the reaction mixture. In the process of the invention, the quantity of the 4-carboxybenzaldehyde (4-CBA) isolated intermediates in the reaction mixture is preferably below 60,000 ppm, more preferably below 50,000, or below 40,000, or below 30,000. The levels of 4-CBA listed are measured as the cumulative amount of 4-CBA in the solid and liquid phase and reported relative to the total weight of solid isolated. In the solid phase alone, the amount of 4-CBA produced by the process of the invention may be 10,000 or less.

A preferred process in accordance with the present invention comprises contacting crude terephthalic acid which is produced by the oxidation of para-xylene with a mixture of nitrogen and oxygen comprising about 5 to 20% oxygen at a temperature of about 120° C. to 190° C. and a pressure of 100 psig to 400 psig. The purification is conducted in the presence of a solvent which is preferably obtained by displacing about 80 to 90% of the mother liquor from the primary oxidation with fresh, wet, acetic acid containing about 4-12% water. The residual mother liquor from the primary oxidation supplies most, if not all, of the necessary catalyst components.

The invention will be further illustrated by the following examples although it will be understood that these examples are included merely for purposes of illustrating some of the embodiments within the scope of the invention.

Referring to the accompanying FIG. 1, p-xylene is introduced via conduit 10 into primary oxidation reactor 12, and aqueous acetic acid solvent having 4-12% water having dissolved therein the catalyst composition of the invention is fed through line 11 to the reactor 12. If desired, the p-xylene, solvent, and catalyst composition charges may be fed to reactor 12 at a plurality of points along the side of the reactor, or fed together through one line. An oxygen-containing gas under pressure is introduced near the bottom of the reactor 12 via conduit 14. The preferred oxygen-containing gas is air or oxygen-enriched air. The flow rate of the oxygen-containing gas to reactor 12 is controlled to maintain between about 2 and 9 volume percent oxygen (calculated on a dry, solvent free basis) in the off-gas which exits the reactor via conduit 16. The reactants in reactor 12 are maintained at an elevated pressure of about 50 to 175 psia to maintain a contained, volatizable reaction medium substantially in the liquid state at the reaction temperature of about 120 to 190° C.

During the course of the oxidation reaction, exothermic heat of reaction and water generated by the oxidation of p-xylene are removed from reactor 12 by vaporization of a portion of the liquid reaction medium. These vapors, known as reactor off-gas, comprise vaporized acetic acid solvent, about 5 to 30 weight percent water, and oxygen-depleted process gas containing minor amounts of decomposition products including catalyst residue, as well as additional carbon dioxide and carbon monoxide generated by the decomposition of acetic acid. The reactor off-gas passes upwardly through the reactor 12 and is conveyed via conduit 16 to the lower portion of water removal column 18 for distillation and recovery of the acetic acid back to the primary oxidation reactor. The crude reaction mixture is discharged from the primary oxidation reactor to a solid/liquid separator 20 into which is fed fresh acetic acid through line 22 to exchange the mother liquor discharged through line 24. The mother liquor containing acetic acid and the catalyst composition is subjected to conventional purification and purging techniques to recover and recycle the catalyst composition to the primary oxidation reactor 12.

The catalyst composition is effective as a catalyst not only in the primary oxidation zone, but also to effectuate post oxidation in secondary reactors to further increase the yield of product.

EXAMPLES 1-7

The following procedure was used as a representative procedure for examples 1-7, with variations noted on the table.

Each of the catalyst solutions set forth in the Table, containing 80 g of a 96% aqueous acetic acid (92% aqueous acetic acid in examples 7) and the noted concentrations of nickel (as $Ni(OAc)_2*4\ H_2O$), manganese (as $Mn(OAc)_2*4\ H_2O$) and bromine (as HBr), were charged to a 300-mL titanium autoclave equipped with a high pressure condenser and an Isco pump. Once the autoclave was pressurize up to 100 psig with nitrogen, the contents were heated to about 160° C., or 163° C. in the case of examples 7, in a closed system (i.e., with no gas flow). Thereafter, the pressure was increased by an additional 240 psi-250 psi using a 50/50 vol % mix of nitrogen and air at a flow rate of about 500 sccm each. Once the autoclave was pressurized to about 340 to 350 psig, the pressure was further increased up to 700 psig using only nitrogen.

At the target pressure, a flow of nitrogen at about 500 sccm and air at about 500 sccm was started and continued to maintain the target pressure throughout the experiment. Once the flow of nitrogen/air at the target pressure was commenced, p-xylene was pumped into the autoclave at a rate of 0.034 mL/min for 136 min. The reaction conditions noted on Table 1 were maintained throughout the experiment. Off-gas samples were taken at 90 min after starting the pumping of p-xylene. Concentrations of CO and $CO_2$ were determined by GC. At the expiration of 136 minutes, the autoclave was cooled under a flow of nitrogen and vent. The reaction mixture was analyzed for the concentration of 4-carboxybenzaldehyde, as determined by high pressure liquid phase chromatography, observed in the solids isolated and in the filtrate. The results are reported in Table 1.

TABLE 1

| Ex. No. | $P_{air}^{eq}$ psia | $P_{tot}$ psig | Co ppm | Ni ppm | Mn ppm | Br ppm | Zr ppm | $CO^{(a)}$ vol % | $CO_2^{(a)}$ vol % | $CO_x^{(a)}$ vol % | Avg. | $CO_x/TPA^{(d)}$ mol/mol | Avg. | 4CBA $(s)^{(b)}$ ppm | Avg. | 4CBA $(t)^{(c)}$ | Avg. |
|---|---|---|---|---|---|---|---|---|---|---|---|---|---|---|---|---|---|
| 1a | 330 | 700 | 0 | 2670 | 1070 | 950 | 0 | 0.00 | 0.02 | 0.02 | | 0.07 | | 5500 | | 7500 | |
| 1b | 330 | 700 | 0 | 2670 | 1070 | 950 | 0 | 0.02 | 0.15 | 0.17 | | 1.03 | | 3800 | | 8900 | |
| 1c | 175 | 350 | 0 | 2670 | 1070 | 950 | 0 | 0.01 | 0.13 | 0.14 | | 0.44 | | 6100 | | 10300 | |
| 1d | 330 | 700 | 0 | 2670 | 1070 | 950 | 0 | 0.00 | 0.13 | 0.13 | | 0.40 | | 6100 | | 8500 | |

TABLE 1-continued

| Ex. No. | $P_{air}^{eq}$ psia | $P_{tot}$ psig | Co ppm | Ni ppm | Mn ppm | Br ppm | Zr ppm | CO[a] vol % | CO$_2$[a] vol % | CO$_x$[a] vol % | Avg. | CO$_x$/TPA[d] mol/mol | Avg. | 4CBA (s)[b] ppm | Avg. | 4CBA (t)[c] | Avg. |
|---|---|---|---|---|---|---|---|---|---|---|---|---|---|---|---|---|---|
| 1e | 330 | 700 | 0 | 2670 | 1070 | 950 | 0 | 0.03 | 0.22 | 0.25 | 0.14 | 0.42 | 0.47 | 9800 | 6300 | 14900 | 10000 |
| Comp 2 | 330 | 700 | 0 | 2670 | 0 | 950 | 0 | 0.00 | 0.02 | 0.02 | 0.02 | N/A[e] | N/A | N/A | N/A | N/A | N/A |
| Comp 3a | 330 | 700 | 0 | 2670 | 1070 | 950 | 65 | 0.70 | 0.13 | 0.83 | | 2.69 | | 6300 | | 11900 | |
| Comp 3b | 330 | 700 | 0 | 2670 | 1070 | 950 | 65 | 0.02 | 0.17 | 0.19 | 0.51 | 0.62 | 1.65 | 4800 | 5600 | 7900 | 9900 |
| 4a | 330 | 700 | 0 | 1280 | 1280 | 1375 | 0 | 0.03 | 0.16 | 0.19 | | 0.69 | | 5000 | | 7500 | |
| 4b | 330 | 700 | 0 | 1280 | 1280 | 1375 | 0 | 0.02 | 0.14 | 0.16 | | 0.65 | | 5000 | | 8400 | |
| 4c | 175 | 350 | 0 | 1280 | 1280 | 1375 | 0 | 0.02 | 0.14 | 0.16 | 0.17 | 0.57 | 0.64 | 4500 | 4800 | 8000 | 8000 |
| Comp 5 | 330 | 700 | 0 | 1280 | 1280 | 1375 | 60 | 0.17 | 0.21 | 0.38 | 0.38 | 1.24 | 1.24 | 4200 | 4200 | 5200 | 5200 |
| 6 | 330 | 700 | 0 | 560 | 2000 | 2050 | 0 | 0.03 | 0.15 | 0.18 | 0.18 | 0.71 | 0.71 | 5600 | 5600 | 9400 | 9400 |
| Comp 7a | 330 | 700 | 1775 | 0 | 1625 | 1625 | 0 | 0.06 | 0.29 | 0.35 | | 0.94 | | 4600 | | 6600 | |
| Comp 7b | 330 | 700 | 1775 | 0 | 1625 | 1625 | 0 | 0.00 | 0.29 | 0.29 | | 0.60 | | 6000 | | 8200 | |
| Comp 7c | 330 | 700 | 1775 | 0 | 1625 | 1625 | 0 | 0.07 | 0.38 | 0.45 | | 1.33 | | 4700 | | 6800 | |
| Comp 7d | 330 | 700 | 1775 | 0 | 1625 | 1625 | 0 | 0.04 | 0.27 | 0.31 | 0.35 | 0.52 | 0.85 | 5200 | 5100 | 6800 | 7100 |

[a]vol % of CO and $CO_2$ detected in the off-gas 90 min after the feed of p-xylene was initiated;
[b]4-CBA concentratian measured in the isolated solid, and does not include the 4-CBA in the mother liquor
[c]concentration of total 4-CBA generated 9 total grams of 4-CBA measures in the solid and in the mother liquor multiplied by $1 \times 10^6$ and divided by the yield (g) of solid isolated
[d]moles of $CO_x$ in the off-gas 90 min after the feed of p-xylene was initiated, relative to the amount (mol) of TPA produced, assuming 100% TPA in the solid.
[a]no solid was isolated in Comp 2.

The stoichiometric molar ratio of nickel, manganese and bromine in Examples 1 was 2.3:1.0:0.6 molar (or 1.0:0.4:0.3 molar normalized to nickel), in Examples 4 was 0.9:1.0:0.7 molar (or 1.0:1.1:0.8 molar normalized to nickel), and in Example 6 was 0.3:1.0:0.7 molar (or 1:3.3:2.3 normalized to nickel).

Examples 1a-1e, 4a-c and 6, which all use a catalyst system consisting of nickel, manganese and bromine, show a marked reduction in solvent burn as seen by the reduced amount of CO and $CO_2$ produced in the course of the oxidation of p-xylene to terephthalic acid, relative to a reaction performed under comparable conditions with a catalyst system consisting of cobalt, manganese and bromine used as a benchmark (Comparative examples 7a-7c). The amount of CO and $CO_2$ released in p-xylene oxidation is proportional to the extent of solvent loss through oxidative means.

Comparative Example 2 shows that terephthalic acid is not produced, under the conditions evaluated (temperature and pressure), in the absence of manganese.

Comparative Examples 3a-3b and 5 show that the addition of zirconium as a fourth catalyst component, even when added to a Ni/Mn/Br based catalyst system with a Br:Mn ratio of less than 1.5, leads to an increase in the amount of CO and $CO_2$ produced, relative to that observed in the absence of Zr (Ex. 1a-1e and 4a-4c and 6).

EXAMPLES 8-16

Examples 8-16 illustrate the effect of stoichiometric molar ratios of the elements nickel, manganese, and bromine on solvent burn and intermediate production, in particular 4-CBA.

Data for Examples Comp 8, Comp 9, 10, Comp 11, Comp 12, and 13 are predicted values obtained from models derived from experiments performed in the same manner as in examples 1-7 using 96% aqueous acetic acid. Results for Examples Comp 14, Comp 15 and 16 are values obtained by an average of 3-4 data points generated in the same manner as in Examples 1 through 7, except that these examples were prepared using 88 wt. % aqueous acetic acid.

TABLE 2

| Ex. | Ni ppm | Mn ppm | Br ppm | Molar Ratio Ni:Mn:Br | Temp ° C. | Yield | CO$_x$[a] (vol %) | CO$_x$/TPA[d] mol/mol | 4-CBA (s)[b] ppm | 4-CBA (t)[c] ppm |
|---|---|---|---|---|---|---|---|---|---|---|
| Comp 8 | 920 | 860 | 2500 | 1:1:2 | 157 | 1.5 | 0.15 | 1.01 | N/A | 44200 |
| Comp 9 | 1750 | 860 | 2500 | 1.9:1:2 | 157 | 2.4 | 0.21 | 0.89 | N/A | 54800 |
| 10 | 1750 | 2500 | 2000 | 0.64:1:0.55 | 157 | 3.8 | 0.15 | 0.40 | N/A | 7600 |
| Comp 11 | 850 | 790 | 2300 | 1:1:2 | 155 | 1.5 | 0.16 | 1.07 | N/A | 48500 |
| Comp 12 | 2100 | 790 | 2300 | 1.9:1:2 | 155 | 2.6 | 0.16 | 0.62 | N/A | 64500 |

TABLE 2-continued

| Ex. | Ni ppm | Mn ppm | Br ppm | Molar Ratio Ni:Mn:Br | Temp ° C. | Yield | CO$_x$[a] (vol %) | CO$_x$/TPA[d] mol/mol | 4-CBA (s)[b] ppm | 4-CBA (t)[c] ppm |
|---|---|---|---|---|---|---|---|---|---|---|
| 13 | 2100 | 2500 | 2300 | 0.77:1:0.63 | 155 | 3.7 | 0.16 | 0.44 | N/A | 20400 |
| Comp 14 | 800 | 750 | 2200 | 1:1:2 | 170 | 1.4 | 0.17 | 1.22 | 52100 | 213000 |
| Comp 15 | 2050 | 750 | 2200 | 2.5:1:2 | 170 | 3.4 | 0.25 | 0.74 | 22200 | 85500 |
| 16 | 2050 | 750 | 850 | 2.5:1:0.78 | 170 | 3.3 | 0.19 | 0.58 | 12100 | 31900 |

[a] vol % of CO and CO$_2$ detected in the off-gas 90 min after the feed of p-xylene was initiated;
[b] 4-CBA concentration measured in the isolated solid, and does not include the 4-CBA in the mother liquor
[c] concentration of total 4-CBA generated (total grams of 4-CBA measured in the solid and in the mother liquor multiplied by 1 × 10$^6$ and divided by the yield (g) of solid isolated)
[d] moles of CO$_x$ in the off-gas 90 min after the feed of p-xylene was initiated, relative to the amount (mol) of TPA produced, assuming 100% TPA in the solid.

In each of the comparative examples, the molar stoichiometric ratio of bromine to nickel or of bromine to manganese was higher than 1.05. Example 10 achieved a simultaneous reduction in solvent burn and 4-CBA content relative to Comparative Examples 8 and 9 having a bromine:manganese ratio higher than 1.5, under the same temperature of 157° C.

Example 13 also achieved a simultaneous reduction in solvent burn per gram of solid isolated and 4-CBA content relative to Comparative examples 11 and 12 at slightly lower reaction temperatures of 155° C.

Likewise, Example 16 achieved a simultaneous reduction in solvent burn per gram of solid isolated and 4-CBA content, and a lower absolute amount of solvent burn, relative to Comparative examples 14 and 15, both of which had a bromine:manganese ratio higher than 1.5, under a more dilute concentration of acetic acid and at a higher oxidation temperature of 170° C.

A comparison of the relatively small variation in solvent burn results between Examples 10, 13, and 16 indicates that the catalyst composition of the invention allows for wide latitude of nickel concentrations.

What I claim is:

1. A process for the oxidation of p-xylene to terephthalic acid comprising oxidizing in the liquid phase a p-xylene composition comprising at least 80 wt. % p-xylene based on the weight of liquid reactants, at a temperature in the range of 120° C. to 250° C. and in the presence of a solvent, a source of molecular oxygen and a catalyst composition comprising less than 5 ppm of zirconium atoms, a source of nickel (Ni) atoms, a source of manganese (Mn) atoms, and a source of bromine (Br) atoms, to form a crude reaction mixture comprising terephthalic acid and incompletely oxidized reaction composition comprising 4-carboxybenzaldehyde (4-CBA) compounds, wherein the stoichiometric molar ratio of bromine atoms to manganese atoms is 1.5 or less, and the amount of nickel atoms is at least 500 ppm.

2. The process of claim 1, wherein said solvent comprises an acetic acid composition.

3. The process of claim 2, wherein said acetic acid composition comprises 2.5 to 15 wt. % water.

4. The process of claim 1, wherein the molar ratio of Br to Ni and the molar ratio of Br to Mn are each 1.5 or less and at least 0.3.

5. The process of claim 4, wherein the molar ratio of Br to Ni and the molar ratio of Br to Mn are each 1.1 or less.

6. The process of claim 5, wherein the molar ratio of Br to Ni and the molar ratio of Br to Mn are each 1.0 or less.

7. The process of claim 6, wherein the molar ratio of Br to Ni is 0.9 or less.

8. The process of claim 1, wherein the molar ratio of nickel atoms to manganese atoms ranges from 0.2:1 to 4:1.

9. The process of claim 8, wherein the molar ratio of nickel atoms to manganese atoms ranges from 0.5:1 to 2.5:1.

10. The process of claim 1, wherein the molar ratio of Br to Mn is 1.1 or less.

11. The process of claim 10, wherein the molar ratio of Br to Mn is 1.0 or less.

12. The process of claim 1, wherein the oxidation temperature is within a range of 140° C. to 190° C. and the oxidation reaction is conducted under a pressure in the range of 50 to 175 psig.

13. The process of claim 1, wherein the catalyst composition contains less than 2 ppm Zr.

14. The process of claim 1, wherein the catalyst composition contains less than 5 ppm cobalt.

15. The process of claim 1, wherein the reaction mixture comprises 40,000 ppm 4-CBA or less.

16. The process of claim 1, wherein the 4-CBA content in the solids is 10,000 ppm or less.

17. The process of claim 1, wherein the ratio of solvent burn is 0.80 moles COx per mole of terephthalic acid produced or less.

18. The process of claim 17, wherein said ratio is 0.70 or less.

19. The process of claim 1, wherein the catalyst composition is free of cobalt atoms.

20. The process of claim 1, wherein the ratio of solvent burn is 0.60 moles COx per mole of terephthalic acid or less, and the total quantity of 4-CBA in the solid and liquid phase is 40,000 ppm or less.

21. The process of claim 20, wherein the total quantity of 4-CBA is 10,000 ppm or less.

* * * * *